United States Patent [19]

Miller et al.

[11] Patent Number: 4,967,034
[45] Date of Patent: Oct. 30, 1990

[54] PROCESS FOR THE ALKYLATION OF ALKANES OR AROMATIC HYDROCARBONS

[75] Inventors: Jorge P. Miller; Miguel F. Kling, both of Bogota, Colombia

[73] Assignee: Energia Andina Ltd., New York, N.Y.

[21] Appl. No.: 403,742

[22] Filed: Aug. 16, 1989

[51] Int. Cl.$^5$ .................. C07C 2/64; C07C 2/66; C07C 2/58
[52] U.S. Cl. .................. 585/446; 585/458; 585/721; 585/730
[58] Field of Search ............ 568/607, 793; 585/446, 585/458, 721, 730

[56] References Cited

U.S. PATENT DOCUMENTS

| | | | |
|---|---|---|---|
| 2,802,884 | 8/1957 | D'Alelio | 568/793 |
| 3,017,441 | 1/1962 | Thomas et al. | 502/159 |
| 3,238,266 | 3/1966 | Skripek | 585/458 |
| 3,239,575 | 3/1966 | Frilette | 585/458 |
| 3,326,866 | 6/1967 | Haag | 585/458 |
| 4,316,997 | 2/1982 | Vaughan | 568/607 |
| 4,317,949 | 3/1982 | Vaughan | 568/607 |
| 4,447,312 | 5/1984 | Angevine et al. | 585/942 |
| 4,849,569 | 7/1989 | Smith | 568/793 |

FOREIGN PATENT DOCUMENTS 0189683  8/1986  European Pat. Off. ............ 585/446

*Primary Examiner*—W. J. Shine
*Assistant Examiner*—J. Saba
*Attorney, Agent, or Firm*—Darby & Darby

[57] ABSTRACT

The invention relates to a process for the vapor phase alkylation of alkanes or aromatic hydrocarbons comprising (a) adsorbing an alkene on a dry cation exchange resin in its hydrogen form and (b) reacting said adsorbed alkene with at least one alkane or at least one aromatic hydrocarbon.

9 Claims, 2 Drawing Sheets

PROCESS FOR THE ALKYLATION OF ALKANES OR AROMATIC HYDROCARBONS

BACKGROUND AND OBJECTS OF THE INVENTION

The present invention relates to a process for the vapor phase alkylation of alkanes or aromatic hydrocarbons.

It is well known to alkylate alkanes or hydrocarbons by the use of acid catalysts. During use said acid catalysts become diluted with polyunsaturated hydrocarbons and, consequently, their activity decreases.

It is generally possible to conduct the alkylation in liquid phase or in vapor phase. The alkylation in liquid phase is, however, extremely slow and can only be carried out with highly reactive reagents. Bernard Loev and John T. Massengale, J. Org. Chem. 22 968 (1957) describe that attempts to alkylate xylene and benzene using a resin catalyst were unsuccessful.

SUMMARY OF THE INVENTION

It is the object of the present invention to provide a simple and less expensive process for the vapor phase alkylation of alkanes or aromatic hydrocarbons.

Said object is achieved by a process which comprises
(a) adsorbing an alkene on a dry cation exchange resin in its hydrogen form and
(b) reacting said adsorbed alkene with at least one alkane or at least one aromatic hydrocarbon.

According to the process of the present invention, no pollution problems arise, whereas in known alkylation processes, for example in the sulfuric acid process, 0.4 pounds of acid per gallon of gasoline are consumed creating severe pollution problems.

BRIEF DESCRIPTION OF THE DRAWINGS

According to the process of the present invention, the alkene is chemically fixed on the resin and reacted with the desired alkane or aromatic hydrocarbon.

DETAILED DESCRIPTION OF THE INVENTION

The steps of chemical adsorption and alkylation can be carried out consecutively or simultaneously by mixing the proper gases and passing them through the cation exchange resin where both reactions occur.

Contrary to the prior art processes, the process of the present invention can be conducted at atmospheric pressure. The temperature for the alkylation generally ranges from 45° C. to 120° C., with 60° to 100° C. being particulary preferred. Higher temperatures than 120° C. tend to form dimers.

The alkene which is absorbed on the cation exchange resin is selected depending on the desired final product. Common alkenes in alkylation processes are propylene and butylene.

Any alkane which can be alkylated may be used in the process of the present invention, for example isobutane and iso-pentane.

Analogously any aromatic hydrocarbon which can be alkylated may be used, for example benzene and toluene. If benzene is reacted with propylene, cumene will be obtained as a final product. Alkylation of toluene mainly results in alkyl-substitution in the para position.

The cation exchange resin which is used in the claimed process is preferably based on polystyrene as matrix and preferably contains sulfonic acid groups as functional groups. For example, if $R-SO_3H$ is used as a cation exchange resin, the following reaction occurs with ethylene:

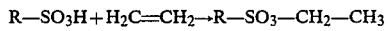

$$R-SO_3H + H_2C=CH_2 \rightarrow R-SO_3-CH_2-CH_3$$

Since the adsorption reaction in step (a) is exothermic, an appropriate cooling is necessary to control the temperature.

In the following, the process of the present invention is described in detail referring to the apparatus of FIGS. 1 and 2.

Figure 1:
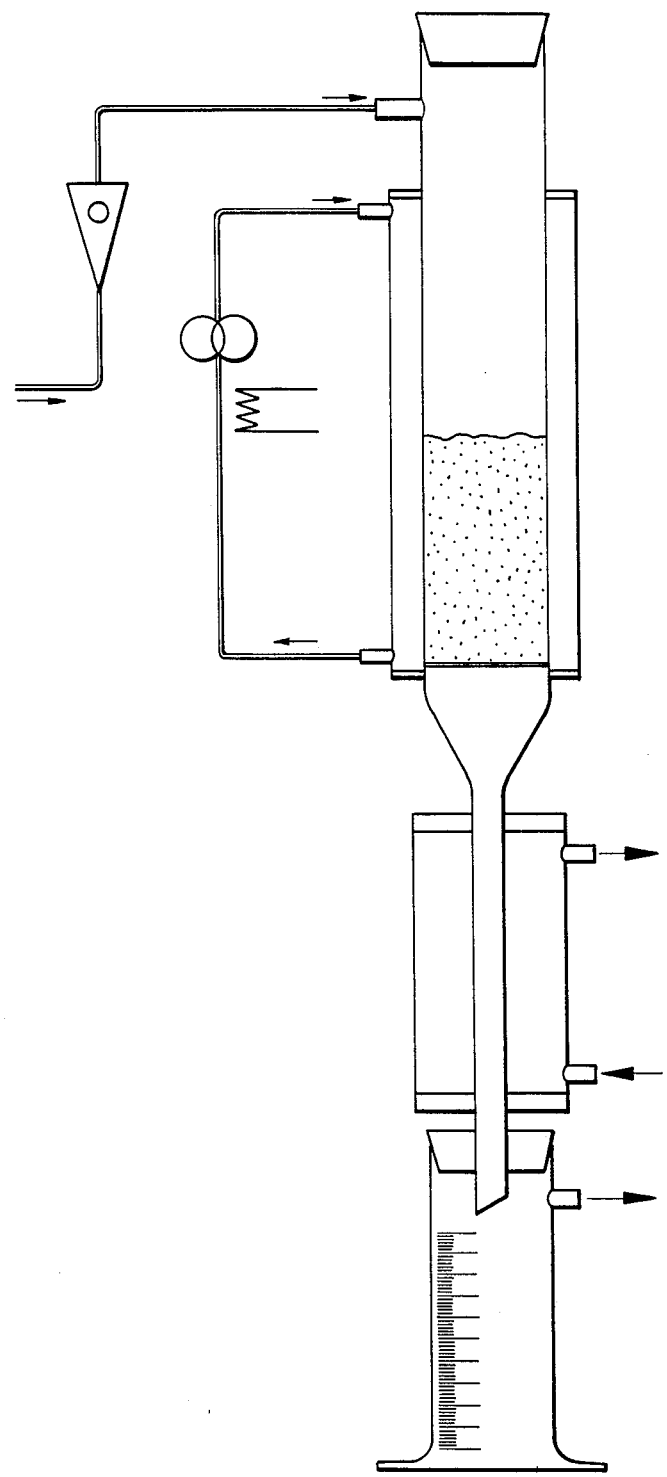
FIG. 1 is a schematical diagram of an apparatus to be used in the present invention.

FIG. 1 shows a tube with a fritted glass which holds the dry ion exchange resin in the hydrogen form. This tube is surrounded by a water jacket whose temperature is kept constant at 60° C.

The gases to be reacted are passed downwards through the resin and the liquid products are collected and cooled at the bottom outlet.

Figure 2:
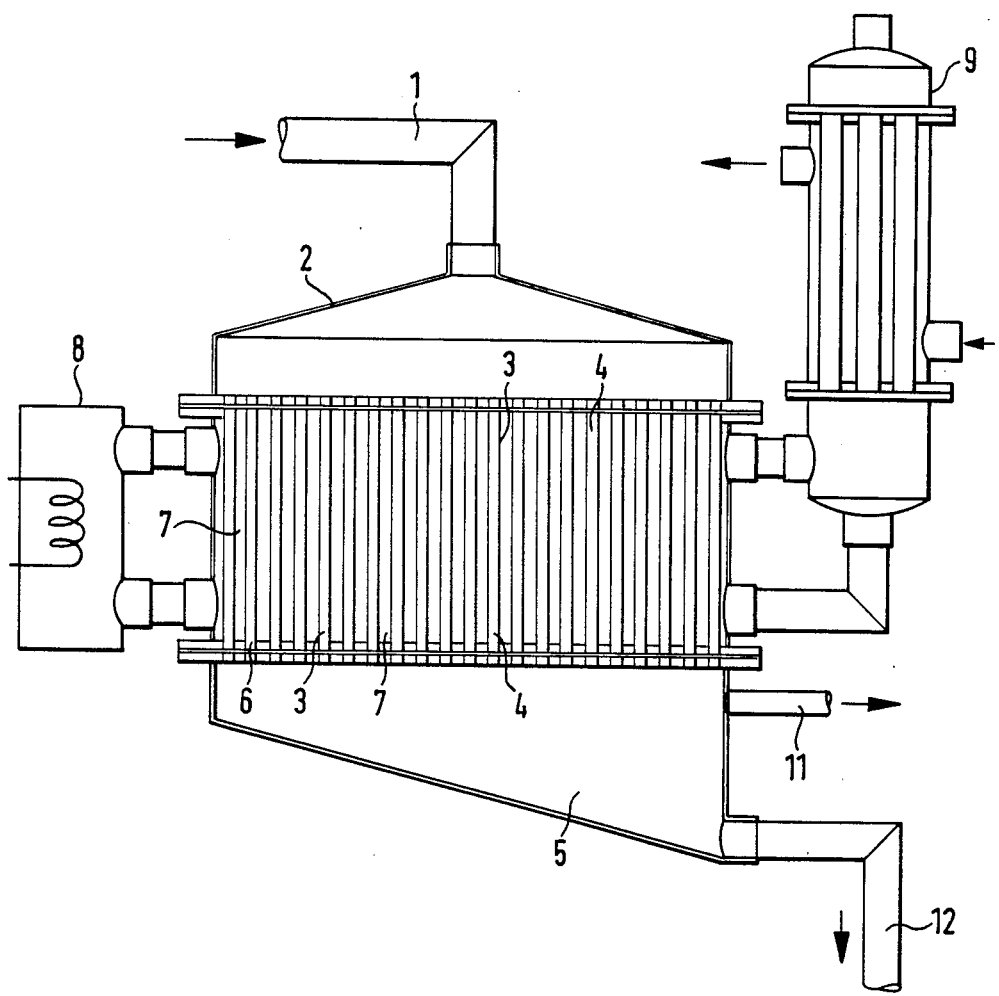
FIG. 2 is a schematical diagram of another embodiment of an apparatus to be used in the present invention.

FIG. 2 shows another embodiment of an apparatus to be used in the present invention. The feed to be alkylated is introduced through feed line 1 into reactor 2 containing tubes 3 filled with catalyst 4. Catalyst 4 is prevented from falling to collector space 5 by sieve 6.

Tubes 3 are surrounded by liquid 7 having a boiling point corresponding to the alkylation temperature required.

Heater 8 provides heat to the liquid to start the reaction and condenser 9 condenses vapors of the boiling liquid 7 to control the exothermic alkylation reaction.

Liquid formed by alkylation drips through the catalyst beds to space 5 and then to pipe 10 where it is collected. Non reacting gases escape through pipe 11.

If propylene and isobutane or butylene and isobutane are alkylated liquid 7 is methanol which boils at 60° C.

If benzene and propylene are alkylated to cumene liquid 7 must boil at about 85° C.

The pressure can be reduced to a vacuum if the reactants have a low vapor pressure to prevent dimerization of the alkenes.

Instead of a vertical flow a horizontal flow of the feed may also be used.

The following examples illustrate the invention.

EXAMPLE 1

In this example the apparatus of FIG. 1 was used.

A gas composition comprising 40% of butylene, 40% of isobutane and 20% of n-butane was passed through a tube having a diameter of 10 mm. The height of the resin was 50 mm.

The temperature of the water jacket was controlled at 60° C.

The gas rate was 12 g/h.

the resin (4 g) used had the following characteristics:

| | | |
|---|---|---|
| Ionic form | | H |
| Shape | | Beads |
| Matrix | | Polystyrene |
| Functional groups | | Sulfonic Acid |
| Bead size distribution (min. 90%) | (mm) | 0.315–1.6 |
| Effective size (±0.03) | (mm) | 0.55 |
| Uniformity coefficient | max. | 1.8 |

-continued

| Bulk Density | (g/l) | 600–700 |
|---|---|---|
| Moisture content | (% wt.) | <0.5 |
| Total capacity in exchange units | (min.) | 4.5 eq/kg. |

The upper part of the resin remained dry while the lower part remained wet, the products dripping down from the wet resin. The major part of the alkylation was performed in the vapor phase.

9 to 9.5 g octane were obtained per hour.

EXAMPLE 2

Using the same equipment with the same amount of resin as in Example 1, propylene gas (95% pure) was bubbled through benzene at a temperature of 59° C. Mixed vapors of propylene and benzene (approximately 50/50 by volume) were passed downwards through the resin.

The temperature of the water jacket was controlled at 85° C.

The gas rate of benzene plus propylene was 20 g/h. The cumene production was 18 g/h.

We claim:

1. A process for the alkylation of alkanes or aromatic hydrocarbons comprising:
   (a) absorbing an alkene on a dry cation exchange resin, said resin being in the hydrogen form
   (b) reacting said absorbed alkene with at least one alkane or at least one aromatic hydrocarbon, and
   (c) maintaining said alkane or aromatic hydrocarbon, and conducting said reacting step, entirely in the vapor phase.

2. The process of claim 1 wherein steps (a) and (b) are conducted consecutively or simultaneously.

3. The process of claim 1 wherein steps (a) and (b) are conducted at atmospheric pressure.

4. The process of claim 1 wherein steps (a) and (b) are conducted at 45° C. to 120° C.

5. The process of claim 1 wherein said alkene is propylene or butylene.

6. The process of claim 1 wherein said alkane is iso-butane and/or iso-pentane.

7. The process of claim 1 wherein said aromatic hydrocarbon is benzene and/or toluene.

8. The process of claim 1 wherein said cation exchange resin has a polystyrene matrix.

9. The process of claim 1 wherein said cation exchange resin has sulfonic acid groups as functional groups.

* * * * *